(12) United States Patent
Beerwerth et al.

(10) Patent No.: US 8,398,621 B2
(45) Date of Patent: Mar. 19, 2013

(54) DEVICE FOR TREATING THE SKIN

(75) Inventors: Frank Beerwerth, Kaltenholzhausen (DE); Dmytro Bohatyrskyy, Frankfurt am Main (DE); Brigitte Harttmann, Niedernhausen (DE)

(73) Assignee: Braun GmbH, Kronberg (DE)

( * ) Notice: Subject to any disclaimer, the term of this patent is extended or adjusted under 35 U.S.C. 154(b) by 861 days.

(21) Appl. No.: 12/515,376

(22) PCT Filed: Nov. 14, 2007

(86) PCT No.: PCT/EP2007/009831
§ 371 (c)(1),
(2), (4) Date: Aug. 24, 2009

(87) PCT Pub. No.: WO2008/058716
PCT Pub. Date: May 22, 2008

(65) Prior Publication Data
US 2009/0326437 A1 Dec. 31, 2009

(30) Foreign Application Priority Data
Nov. 18, 2006 (DE) .......................... 10 2006 054 468

(51) Int. Cl.
*A61B 18/18* (2006.01)

(52) U.S. Cl. .................. 606/9; 604/20; 607/88; 607/89; 607/90; 607/91

(58) Field of Classification Search ...................... 604/20; 606/9; 607/88–91
See application file for complete search history.

(56) References Cited

U.S. PATENT DOCUMENTS

| 2002/0062142 | A1 | 5/2002 | Knowlton | |
|---|---|---|---|---|
| 2005/0045189 | A1 | 3/2005 | Jay | |
| 2005/0049657 | A1 | 3/2005 | Jay | |
| 2005/0177139 | A1 | 8/2005 | Yamazaki et al. | |
| 2005/0251118 | A1* | 11/2005 | Anderson et al. | 606/9 |
| 2006/0020260 | A1 | 1/2006 | Dover et al. | |
| 2006/0058712 | A1* | 3/2006 | Altshuler et al. | 601/15 |
| 2008/0190655 | A1 | 8/2008 | Davoine et al. | |
| 2010/0276609 | A1 | 11/2010 | Fertner et al. | |

FOREIGN PATENT DOCUMENTS

| WO | WO2004/037287 | 5/2004 |
|---|---|---|
| WO | WO2004/080279 | 9/2004 |
| WO | WO2005/009266 | 2/2005 |
| WO | WO2005/092438 | 10/2005 |
| WO | WO2005/110266 | 11/2005 |
| WO | WO2005/112815 | 12/2005 |
| WO | WO2006/005443 | 1/2006 |
| WO | WO2006/122136 | 11/2006 |
| WO | WO2006/134426 | 12/2006 |

* cited by examiner

*Primary Examiner* — Tod T Van Roy
(74) *Attorney, Agent, or Firm* — David K Mattheis; Kim W Zerby

(57) ABSTRACT

A device for treating the skin, for instance for removing body hair. The device includes a working head, which includes an irradiating device for irradiating the skin surface to be treated, preferably by means of light; a contact surface surrounding the irradiating device for supporting the working head on the skin surface; and a safety device for controlling the irradiation and/or for providing a safety signal. The safety device includes a recording device for recording the support of the working head on the skin surface. The contact surface defines a bell-like pressure and/or sound chamber and the recording device encompasses an impermeability sensor device for determining the over-pressure and/or sound impermeability of the pressure and/or sound chamber.

20 Claims, 2 Drawing Sheets

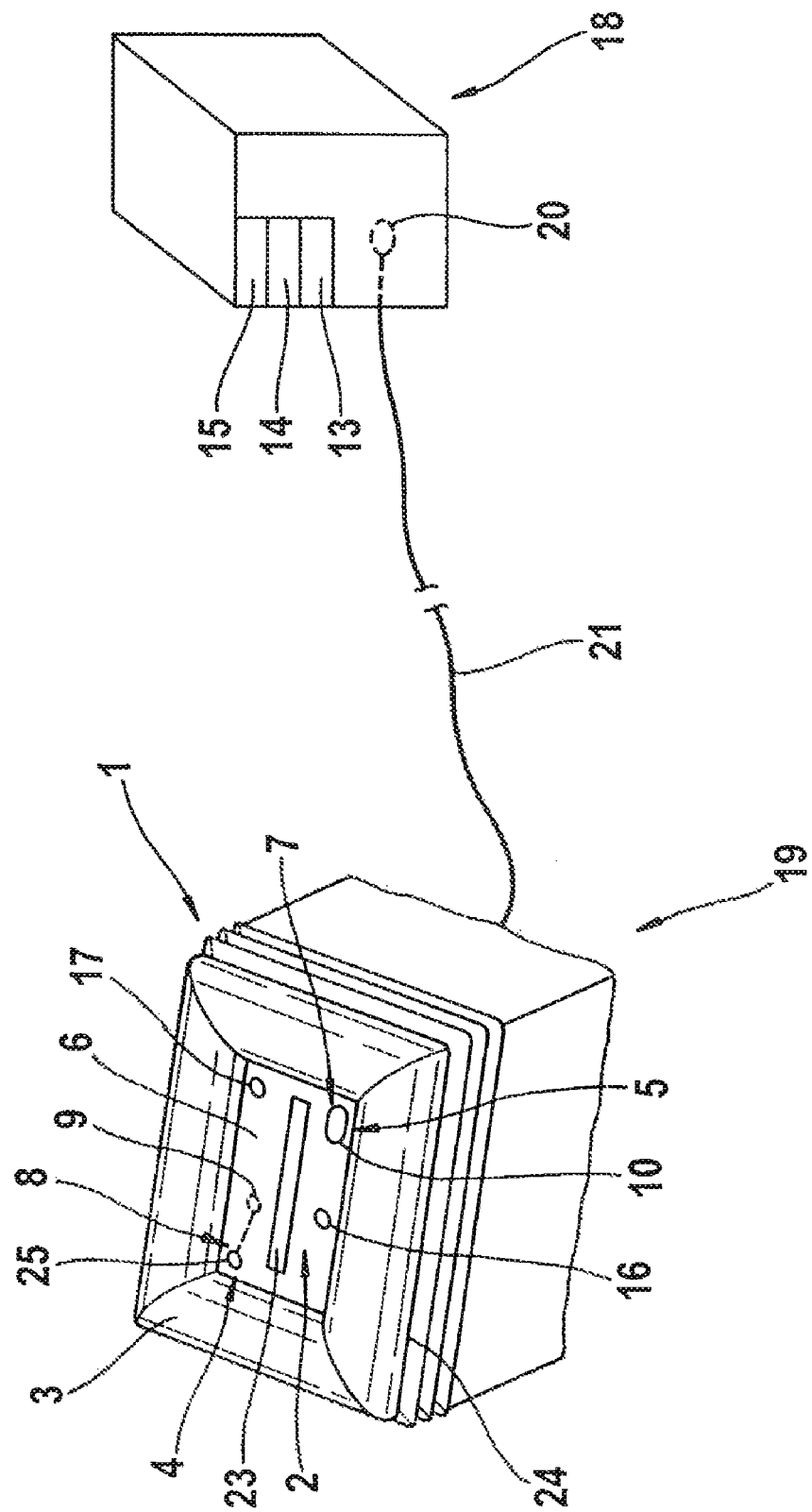

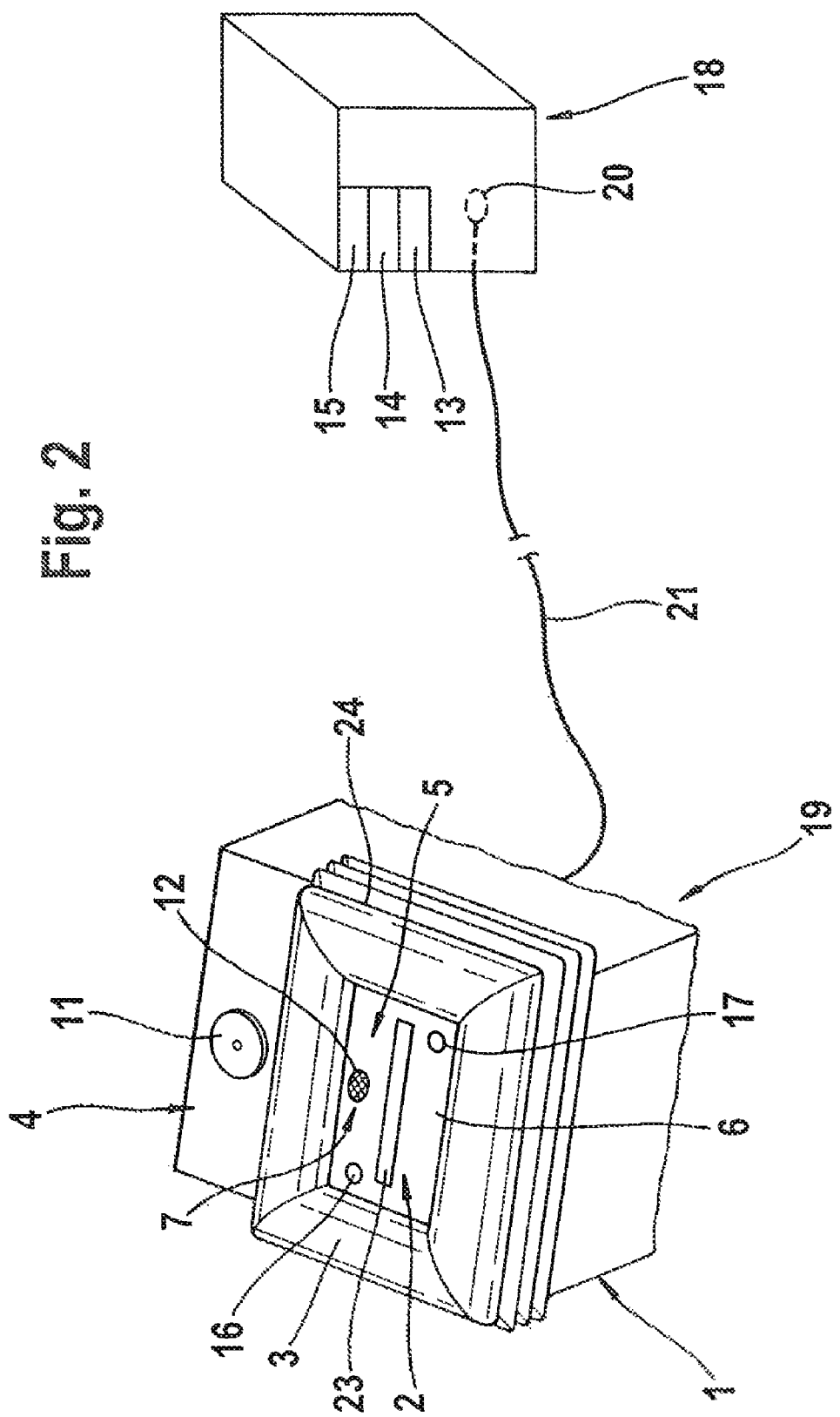

DEVICE FOR TREATING THE SKIN

TECHNICAL FIELD

The instant invention relates to a device for treating the skin, in particular for influencing the growth and/or for removing body hair.

BACKGROUND

In addition to the common mechanically operating epilators, devices for removing body hair, which irradiate the skin surface in particular with electromagnetic irradiation of a suitable wavelength, in particular laser light or pulsed light, so as to damage the hair roots and follicles, which are embedded in the skin or which are located underneath the skin, respectively, are used to an increasing extent to remove body hair. Wavelengths in the range of from 600 to 1100 nm and pulse lengths in the range of from 20 to 500 ms can hereby be used in particular, so that the hair and the immediately surrounding tissue layers are subjected to a photothermolysis, by means of which the structure of the hair and follicle cells can be changed and the hair growth can be reduced.

Due to the fact that high energy densities in the range of from 1 to 50 $J/cm^2$ are used hereby, proper use is required. Such domestic equipment thus requires special safety measures.

Concerning this matter, different safety measures have already been proposed. US 2005/0049657 and US 2005/0045189 in each case combine equipment for irradiating body skin or for reducing body hair, respectively, where the operator can set different device parameters so as to adjust the irradiation to the personal requirements. To avoid dangerous operating errors, the devices comprise a safety device, which, in response to the corresponding setting of a device parameter, has the effect that upper limits, which correspond to other device parameters, cannot be exceeded so as to limit the total applied energy content (in particular per time and per area). US 2005/0177139 A1 describes a device for removing body hair, where the speed of movement, at which the working head is moved across the skin surface, is recorded by means of a roller, which serves as a speed sensor and which rolls on the skin surface. The irradiation intensity is changed as a function of the recorded speed of movement, the irradiation intensity is reduced in particular when the working head is moved too slowly, so as to avoid an excessive irradiation of the skin surface. A similar safety device is described in US 2006/0020260, which also records the speed of movement of the working head by means of a speed sensor and which correspondingly controls the laser irradiation source. The corresponding sensor is thereby preferably to be embodied so as to operate in an optical manner and is to simultaneously record the proximity of the skin to the sensor so that the laser source can be turned off as soon as the working head with the sensor is moved too far away from the skin, which is to be treated. A hair removal or hair reducing device, respectively, comprising a similar safety device is described in WO 2006/005443.

A device for the application of light onto the skin is described in WO 2005/009266 A1, which encompasses a treatment head comprising a recess, from which the light is emitted and in which the air pressure can be reduced by means of a pump. The device also encompasses a pressure measuring unit, which measures the air pressure in the recess. Above an air pressure threshold value, a control means prevents activation of the light emission as such pressure means that the device is not sealed against the skin surface to be irradiated. The fact that the skin is thereby sucked into the recess also leads to an improvement of the characteristics of the skin with reference to the absorption of light irradiation.

SUMMARY

In one aspect, the sound permeability or over-pressure permeability, respectively, of the contact surface surrounding the irradiating device is checked for the purpose of monitoring the correct engagement of the working head against the surface to be treated. This is based on the idea that gas over-pressure can escape easily at a gap between the contact surface of the working head and the skin surface and that sound can escape or enter, respectively, easily, whereas gas and/or sound cannot easily escape or enter, respectively, in response to a close contact. A gap formation between the contact surface and the skin, which is to be treated, is thereby at the same time the criterion for an early detection of possible danger, because electromagnetic irradiation, in particular intensive laser light can escape at a gap, which, however, is not the case in response to a close contact. Provision is made for the contact surface of the working head to define a pressure and/or sound chamber, which can be placed onto the skin surface in particular in a bell-like manner and the recording device encompasses an impermeability sensor device for determining the over-pressure and/or sound impermeability. The working head is thus embodied around the irradiating device sort of like a pressure or sound bell, respectively, which together with the skin surface located thereon, defines a space, which acts in a sound-reducing and/or pressure-insulating manner relative to the environment, wherein it can already be sufficient when the insulating effect is available only to a limited degree. By measuring the degree of the sound impermeability or over-pressure impermeability, respectively, of the space enclosed by the contact surface, it can be determined whether the working head correctly rests on the skin and the irradiation of the skin with electromagnetic irradiation can be controlled accordingly as a function of the close contact of the contact surface. The used electromagnetic irradiation can in particular be irradiation in the visible light spectrum, in the IR range or in the UV range. A bell-like sound chamber is not to indicate that the chamber has a bell-shape. A chamber formed by a plane working head, by a projecting contact surface, which surrounds the plane working head (which is formed, for instance, in the shape of a closed polygonal or oval or round ring, respectively) and the skin is to be included by "bell-like" or by the terms "pressure bell" or "sound bell", respectively.

In another aspect, provision is made for a pressurization device, by means of which an over-pressure can be generated in a specific manner in the pressure or sound chamber, respectively, which is surrounded by the contact surface. Provision can hereby in particular be made for a pressurization device in the form of an air flow generator, by means of which a continuous or pulse-like air flow can be introduced into the pressure and/or sound chamber. An over-pressure can hereby be generated in the pressure or sound chamber, respectively, in response to a conventional, gap-free contact of the working head on the skin surface to be treated. However, in the event of a gap between the contact surface and the skin surface, the pressure escapes and a corresponding pressure drop occurs. If an air flow of a given over-pressure is thus introduced into the pressure and/or sound chamber against the ambient pressure via an air outlet, this leads to the formation of an over-pressure in the pressure and/or sound chamber, which can be measured by means of a pressure sensor of the impermeability sensor device, when the contact surface, which defines the pressure and/or sound chamber, abuts closely on the skin.

The pressure ratios or the pressure fluctuations, respectively, can be recorded in different ways. For example, provision can be made for an indirectly operating recording device, which records the stress and/or the power consumption of the pressurization device, for example. In the event that the air flow generator introduces air into the pressure or sound chamber, respectively, for example in response to a gap-free contact, the air generator operates against a higher resistance, while a lower resistance must be overcome in response to the appearance of a gap, which can be recorded by means of the power input of the air generator, for example. In the alternative, the air quantity, in particular the air flow, which is introduced into the pressure or sound chamber, respectively, could also be recorded. However, in a preferred implementation, the pressure ratios and in particular the pressure fluctuations are recorded by means of a pressure sensor arranged in the chamber and surrounded by the contact surface. In some cases, the pressure sensor is in second chamber connected to the first, and formed by the contact surface itself. For example, the pressure sensor can be arranged in a hollow cushion that makes up the contact surface. The pressurization device comprising an air flow generator and a pressure sensor can, in particular, be arranged in the chamber formed by the hollow cushion. The appearance of a gap and thus the danger potential of escaping irradiation (for instance of intensive laser light) can be recorded immediately and without delay by means of such a pressure sensor.

In the alternative or in addition, the impermeability sensor device can encompass an acoustic sensor system, by means of which the sound transmission through a gap between skin surface and contact surface or a gap, which is not present there, respectively, can be recorded. For this, the impermeability sensor device advantageously encompasses at least one sound generator on one side of the contact surface and at least one sound detector on an opposite side of the contact surface. Through this, it can be determined in an accurate manner to which degree the sound bell surrounding the irradiating device is sound-proof. In the event that a gap appears, sound can easily escape or enter, respectively, while the sound passage is accordingly obstructed in response to a correctly supported contact surface.

The arrangement of the at least one sound generator and of the at least one sound detector can be made in different manners. For example, the sound generator could be arranged within the chamber, which is surrounded by the contact surface, so that the escaping sound can be recorded by means of a sound detector, which is arranged on the outside. In one aspect, however, the at least one sound generator is arranged outside of the pressure and/or sound chamber, while the at least one sound detector is arranged within said pressure and/or sound chamber. In so doing, the impact of ambient noises and background sound can be reduced considerably. By arranging the sound detector within the pressure or sound chamber, respectively, it can be accurately recorded to which degree sound can penetrate through a possibly existing gap. In the event that the working head rests correctly on the skin surface to be treated, a clearly noticeable drop of the sound amplitude of the sound generated by the sound generator takes place, while the amplitude drop will be considerably reduced in the event that there is a gap between the contact surface of the working head and the skin surface, which is to be treated. If applicable, a sound generator could also be completely done without, because the ambient noise entering into the pressure or sound chamber, respectively, can be recorded in response to sufficient ambient or background noises, respectively. However, the afore-described embodiment comprising the arrangement of a sound generator outside of the contact surface is preferred, because the appearance of gap can be recorded herewith a high accuracy independent on of background noises.

In some cases, one sound generator is hereby sufficient. However, a plurality of sound generators can be arranged at different sections of the contact surface. Gaps appearing at different locations can be determined in a simple and accurate manner via a plurality of sound generators distributed across the periphery of the contact surface.

In some implementations, the sound generators are oriented toward an edge of the contact surface and emit the sound specifically to the edge.

The evaluation of the signals of the pressure recording device and/or of the sound recording device can take place in different ways. For example, an absolute value of the pressure prevailing in the pressure or sound chamber, respectively, and/or an absolute value of the sound level across the contact surface could be recorded, wherein this absolute value is then compared to a corresponding setpoint value so as to decide whether or not the contact surface rests correctly and impermeably on the skin surface. The pressure recording device can measure the pressure in the pressure and/or sound chamber as well as the relative pressure against the ambient pressure, which makes the device insensitive to different ambient pressures or changing ambient pressure ratios, in particular in the event that the over-pressure, which is to be measured, is low. In some implementations, the evaluation unit is provided for the purpose of monitoring a change of the pressure signal or of the sound signal, respectively, and to decide by means of the quantity and/or quality of an appearing change, whether a lifting of the working head, which endangers the safety of the use of the device, takes place. For this, the evaluation unit can in particular compare an appearing pressure drop and/or an appearing sound level rise or drop, respectively, to corresponding threshold values, with reference to the amount. In the event that an excessive pressure change takes place and/or in the event that an excessive sound level change takes place, the evaluation unit emits a safety signal, which indicates a lifting of the working head that may endanger irradiation safety.

The safety signal derived from the sound impermeability or pressure impermeability test, respectively, can be used in different ways. In one embodiment, an acoustic, visual and/or mechanical, preferably a vibration signal, can be emitted for example, which indicates to the operator that the working head is guided correctly (or incorrectly) across the skin surface. In one implementation, the safety device is connected to a control device, which automatically controls the irradiation emitted by the irradiating device as a function of a signal of the safety device, which in particular reduces it or completely turns it off in the event that an unconventional use of the working head is detected. For instance, the irradiation is thus reduced or turned off, respectively, as soon as the afore-mentioned impermeability sensor device records a corresponding pressure change and/or a corresponding sound level change. The control device can, in particular, immediately turn off the irradiation source as a function of a corresponding signal of the impermeability sensor device.

To provide for an error-free operation of the safety device even when treating difficult body surfaces comprising larger contour unevenness, the contact surface of the working head is resilient, in particular to be resistant to pressure, according to the type of a cushion or follicle. The contact surface can, in particular, be formed at least partially by a protruding ring, which has a contour-fittable front side. For this, the contact surface can be placed onto the skin surface without a gap, even in response to unevenly formed body surfaces and can be guided beyond them. These limb surfaces, which are difficult for devices for removing body hair, are bony parts, such as the surface of the back of the hand/wrist or the shinbone area. The cushion-like, pressure-resistant embodiment of the contact surface of the working head hereby not only makes it possible to avoid the undesired and, if applicable, dangerous escape of irradiation at such body parts, but also effects a reliable operation of the afore-described safety device in response to treating such difficult body parts, because the deformable embodiment of the contact surface can also hold the pressure prevailing in the pressure or sound chamber, respectively, or can reduce the sound transition in response to a correct attachment of the working head there. A further advantage is that the contact surface can surround a relatively large chamber, without the appearance of a gap formation each time in response to body surface unevenness, because the pressure-resistant embodiment of the contact surface can also compensate for larger unevenness. This makes it possible for the irradiation surface to be relatively large, thus providing for an efficient operation or treatment, respectively. The cushion can thereby be embodied, for instance, as a ring, which is designed so as to be angled (for instance, triangular, rectangular, pentagonal, etc.) or as a round, in particular circular or oval ring. The cushion can be made from flexible foam, for instance from a polyurethane foam, for instance, and can also encompass a jacket made of an elastic, water-tight material. The cushion can also be embodied to be hollow, for instance in that the contact surface is made from an elastomer material, for instance latex. The interior of the cushion can be connected to the pressure and/or sound chamber via openings and can thus be a part of the pressure and/or sound chamber. As already mentioned, the pressurization unit can then be arranged in the hollow interior of the cushion with an outlet of the air flow generator and an inlet of the pressure sensor. A skin lotion, which is applied when using the described device, can then not easily penetrate the inlet of the pressure sensor, for instance, and clog this opening, which would lead to a malfunction of the device, because it would no longer be possible to measure the resulting over-pressure in the pressure and/or sound chamber.

To reach a further increase of the safety of the use of the device, the safety device can furthermore encompass a skin recording sensor, by means of which it can be recorded whether the surface supported on the contact surface of the working head is a skin surface. In the event that the skin recording sensor records, for example, that the working head is not attached to a skin surface, a safety signal can be provided and/or the afore-mentioned control device can reduce or turn off the irradiation, respectively, so as to prevent an undesired surface irradiation. Through this, it can be prevented, for example, that the surfaces of textiles or clothing are damaged when the working head is moved across such a surface. Advantageously, the skin recording sensor can be embodied so as to operate in a contact-free manner, a capacitive and/or optical sensor can, in particular, be provided as the skin recording sensor.

In the alternative or in addition, provision can be made for a motion sensor, in particular a speed sensor, by means of which the movement, in particular the speed is recorded, at which the working head is guided across the surface, which is to be treated. This motion sensor can be embodied in fundamentally different ways, for example it can operate mechanically and can comprise a feeler wheel. Alternatively, the motion sensor can also be embodied so as to operate in an optical and/or capacitive manner in which the motion sensor thereby records the movement of the working head across the surface, which rests on the contact surface thereof. The motion sensor can also operate by means of sonar waves or ultrasound and can carry out measurements according to the Doppler principle, in particular.

The motion signal, in particular the speed signal can be used advantageously by the control device for the purpose of automatically controlling the irradiation emitted from the irradiating device. The energy density of the irradiation, for example, can be reduced with a decreasing speed and/or when a minimum speed is undershot so as to avoid injuries. In the alternative or in addition, the irradiation intensity can be increased with an increasing speed. The irradiation can, in particular, be completely prevented when no movement at all is recorded any longer.

In one aspect, the working head of the device can form a separate component, which is connected to a base part of the device via a power line, in particular in the form of a light conducting cable. Through this, the operating head can be embodied so as to be particularly compact, whereby the handling is simplified. The irradiation source, in particular in the form of a laser source, can be arranged in the base part, from which the generated light is guided via the light conducting cable into the working head, from where the light is emitted across the afore-mentioned irradiating device. In another aspect, however, the working head can also form a section of the entire device, that is, the irradiating source in particular in the form of a laser unit can also be integrated into the working head.

In another aspect, the device encompasses a liquid applicator for applying liquid to the skin. Such a liquid applicator is described, for instance, in WO 2005/110266 A2.

Another aspect includes an exchangeable attachment for the described device, wherein the attachment comprises at least the contact surface, which defines the pressure and/or sound chamber. This attachment can be mounted onto the working head so as to form the described device. Such an attachment provides the advantage that provision can be made, for instance, for each operator to have his own attachment, which is sensible for hygienic reasons, or that provision is made for different attachments comprising different geometries of the contact surface, so as to even better adapt to the conditions of the skin surface, which is to be treated.

Preferably, the use of a safety device with a simple design is to obtain an increased operational safety, which also provides for the home use of the device without any danger. Preferably, the safety device is to also provide for a problem-free use at irregularly formed, bony body surfaces and is not to limit the working surface of the working head too much so as to provide for an efficient use through large treatment surfaces.

These and other features become evident from the following description of preferred exemplary embodiments and from the corresponding drawings, either alone and also in subcombination, independent on the combination thereof in the claims.

BRIEF DESCRIPTION OF THE DRAWINGS

FIG. 1 shows a perspective illustration of the working head and of the base part connected thereto of a device for reducing body hair, where the safety device encompasses a pressure recording device at the working head and FIG. 2 shows a perspective illustration of the working head and of the base part connected thereto of a device for reducing body hair, where provision is made on the working head for a sound recording device.

DETAILED DESCRIPTION

The irradiation epilator shown in FIG. 1 comprises a base part 18 as well as a hand piece 19, which comprises a working head 1 or which is embodied as working head 1, respectively. See FIG. 1. In the illustrated embodiment, a light source 20, in particular in the form of a laser source, the light irradiation of which is guided via a light conductor 21 to the hand piece 19, which is connected to the base part 18 through said light conductor 21, is thereby arranged in the base part 18. As an alternative to this configuration, the light source 20 could also be integrated into the hand piece 19 or the hand piece 19 could be combined with the base part 18 to form a common device component, respectively.

At the working head 1, the light, which is fed or generated, respectively, is emitted via an irradiating device 2, which can comprise corresponding optical elements and which, in the illustrated embodiment, comprises a preferably slot-shaped light emission area 23, which can also be embodied in other emission geometries, via which the laser irradiation can be emitted to irradiate the skin, which is to be treated.

Said light emission area 23 is surrounded by a bead-shaped closed ring 24, which, in its entirety, defines a projecting contour and which defines the pressure and/or sound chamber 6 in its interior, in which the light emission area 23 is arranged, wherein the pressure and/or sound chamber 6 can be coupled to the skin surface, which is to be treated, in a bell-like manner. The front side of the ring 24 thereby forms a contact surface 3, by means of which the working head 1 can be attached to the skin surface, which is to be treated, in a conventional manner. Said contact surface 3 is thereby embodied so as to be pressure-resistant and contour-fittable so that it can adapt to the body parts, which are contoured in a relief-like manner. In an undeformed embodiment, the contact surface 3 defines a plane surface, which, however, can adapt to peaks and troughs in the body surface. In the alternative, the contact surface 3, however, can also define a concave or convex surface. Due to the fact that many geometrically problematic body parts are formed in a convex or concave manner (in particular the legs, the ankle regions or the forearm region), a concave or convex contact surface 3, respectively, can support a close support on such convex or concave skin surfaces, respectively. The ring 24 can thereby be embodied as a removable attachment so that, depending on the use, an operator can chose for instance between a ring 24 comprising a plane contact surface 3 and a ring 24 comprising a concave or convex contact surface 3. For this, the ring 24 as a whole can be embodied according to the type of an elastic tube. In the embodiment illustrated in FIG. 1, the base section of the ring 24 is embodied according to the type of a bellows, see FIG. 1. In the alternative or in addition, the front section of the ring 24 can be embodied from a pressure-resistant material, which can be deformed in a foam-like manner. In particular, the ring 24 can have an inner cavity. This inner cavity can be connected to the pressure and/or sound chamber by means of openings, which are located in the interior at the annular bead so that this inner cavity of the ring 24 is a chamber, which is connected to the pressure and/or sound chamber and which is thus a part of the pressure and/or sound chamber. The ring can be made of an elastomer material so as to ensure the required pressure resistance.

To record the support of the contact surface 3 on the body part, which is to be treated, and to identify a gap formation between the contact surface 3 and the skin surface, a recording device 5, which is part of safety device 4 and comprises an impermeability sensor device 7, is assigned to the working head 1. In the embodiment illustrated in FIG. 1, said impermeability sensor device 7 comprises a pressurization device 8 in the form of an air flow generator 9, the air outlet 25 of which can be seen in FIG. 1 and which opens into the pressure or sound chamber 6, respectively, within the ring 24. A pressure sensor 10, by means of which the over-pressure, which builds up by means of the supplied airstream, can be recorded, is furthermore arranged in the pressure or sound chamber 6, respectively, which is defined by the ring 24. As an alternative to the illustrated embodiment, the air outlet 25 and/or the pressure sensor 10 can be arranged below a ring 24, which is formed so as to be hollow. Air can thereby then flow from openings located on the inside of the ring 24, which are typically not covered by the skin in response to a close contact, so that the hollow interior of the ring 24 is a part of the pressure and/or sound chamber, because a pressure balance is established between the hollow interior and the chamber surrounded by the ring 24 in response to a close contact.

The signals of the pressure sensor 10 are fed to an evaluation unit 14, which compares the resulting pressure changes to corresponding threshold values by means of a comparator unit 1. In the event that an excessive pressure drop is determined, which always results when the contact surface 3 is not correctly supported on the skin surface, the light source 20 is immediately lowered (meaning that its intensity is reduced or turned off) by means of a control device 15, which is connected to the evaluation unit 13, so as to exclude a danger potential by means of the irradiation, which is emitted by the irradiating device 2. The pressure sensor 10 can thereby measure the pressure prevailing in the pressure and/or sound chamber 6 as relative pressure to the ambient pressure so that the pressure measurement must not detect changes of an absolute pressure and is independent of the ambient pressure ratios.

In the alternative or in addition to such a pressure or pressure change recording device, the working head 1 can also have a sound permeability recording device, as is shown in the embodiment of the working head 1 illustrated in FIG. 2. A sound generator 11 can hereby in particular be arranged at the working head 1 outside of the pressure and/or sound chamber 6, that is, on the outside of the ring 24, while, on the other hand, provision is made in the pressure and/or sound chamber 6 for a sound detector 12, for example in the form of a microphone. Advantageously, the sound generator 11 is thereby arranged in such a manner that the sound generated by it is emitted to the contact surface 3. Even though FIG. 2 only shows one such sound generator 11, provision can be made for a plurality of sound generators 11 and/or for a plurality of sound detectors 12. In particular, they can be arranged so as to be distributed across the periphery of the ring 24. In the rectangular embodiment of the ring 24 illustrated in FIG. 2, it would lend itself to position a sound generator 11 at each of the four limbs of the ring 24. Optionally, the at least one sound generator 11, however, can also be arranged at the base part 18, for example.

The sound detector 12 is also connected to the evaluation unit 13 of the control device 15, which compares the sound level drop between the sound generator 11 and the sound detector 12 to corresponding threshold values by means of the comparator unit 14, for instance. In the event that the contact surface 3 rests correctly on the skin, which is to be treated, a substantial amplitude drop will occur from the sound generator 11 to the sound detector 12, while this amplitude drop will be considerably less when a gap is present at the corresponding contact surface 3. In this case, when a sufficient sound level drop does not occur, the control device 15 can also immediately lower the light source 20 so as to avoid danger.

Provision can furthermore be made on the working head 1 for a skin recording sensor 16, which is arranged, for instance, between the light emission area 23 and the ring 24, as it is shown in FIGS. 1 and 2. By means of the skin recording sensor 16 it is determined whether the surface resting on the contact surface 3 is a skin surface. In the event that this is not the case, for example when the working head 1 is moved across a piece of textile or a piece of clothing, respectively, the control device 15, which is connected to the skin recording sensor 16, can also lower the light source 20 (meaning that its intensity is reduced or turned off). Said skin recording sensor 16 can operate in a capacitive manner and/or can be embodied in an optical manner.

FIGS. 1 and 2 furthermore show a motion sensor 17, which records the movement of the working head 1 across the surface, which is to be treated, and in particular the speed thereof according to the type of a PC mouse sensor. The control device 15, which is connected to the motion sensor 17, can control the light source 20 as a function of the recorded movement speed, in particular lower the light source 20 as soon as a minimum speed is undershot. The motion sensor 17 can also be embodied in different ways. Provision can be made, for example, for a sensor, which operates in a mechanical manner. In the alternative or in addition, provision can be made for a motion sensor 17, which operates in an optical and/or capacitive manner.

The invention claimed is:

1. A device for treating the skin, the device comprising:
 a working head comprising:
   an irradiating device for irradiating a surface of the skin to be treated with electromagnetic radiation;
   a contact surface positioned about the irradiating device and configured to support the working head on the surface of the skin; and
   a safety device comprising a monitor that monitors engagement of the contact surface of the working head against the surface of the skin,
 wherein the working head defines a chamber about the irradiating device, and
 wherein the monitor comprises an impermeability sensor that is responsive to a change within the chamber, the change consisting of an increase in sound permeability, as indicative of whether the contact surface is properly engaged, and comprises a sound generator positioned outside of the chamber and a sound detector positioned inside of the chamber.

2. The device of claim 1, wherein the safety device is configured to control the radiation from the irradiating device.

3. The device of claim 1, wherein the safety device is configured to provide a safety signal.

4. The device of claim 1, wherein the sound generator is arranged to direct sound toward an edge of the contact surface.

5. The device of claim 1, further comprising additional sound generators positioned outside of the chamber.

6. The device of claim 1, further comprising an evaluation unit operatively coupled to the impermeability sensor, the evaluation unit responsive to a change in impermeability of the chamber.

7. The device of claim 6, wherein the evaluation unit is responsive to a change in sound level in the chamber.

8. The device of claim 7, wherein the evaluation unit comprises a comparator operable to compare the change in sound level to a threshold value and to provide a safety signal when the change in sound level exceeds the threshold value.

9. The device of claim 1, wherein the safety device is coupled to a controller operable to reduce the irradiation emitted by the irradiating device based on a signal from the impermeability sensor.

10. The device of claim 1, wherein the contact surface comprises a resilient material.

11. The device of claim 1, wherein the contact surface is a surface of a bellows.

12. The device of claim 1, wherein the contact surface is arranged to conform to contours.

13. The device of claim 1, wherein the impermeability sensor is positioned at a base of the chamber.

14. The device of claim 1, wherein the contact surface is removably coupled to the irradiating device.

15. The device of claim 1, wherein the monitor comprises a skin recording sensor capable of determining if a surface touching the contact surface is a skin surface.

16. The device of claim 15, wherein the skin recording sensor is operable to determine if the surface touching the contact surface is a skin surface without the skin recording sensor contacting the surface touching the contact surface.

17. The device of claim 1, wherein the working head further comprising a motion sensor.

18. The device of claim 17, wherein the motion sensor comprises a speed sensor operable to assess speed of the working head across the surface of the skin.

19. The device of claim 18, wherein the working head further comprises a control device operable to control the radiation emitted by the irradiating device as a function of kinetic momentum of the working head.

20. The device of claim 1, wherein the device further comprises a liquid applicator for applying a liquid to the skin.

* * * * *